United States Patent [19]

Ohlendorf et al.

[11] Patent Number: 4,814,345

[45] Date of Patent: * Mar. 21, 1989

[54] 1-PHENYL-2-AMINOCARBONYLINDOLE COMPOUNDS, PREPARATION THEREOF AND PHARMACEUTICAL COMPOSITIONS CONTAINING THEM

[75] Inventors: Heinrich-Wilhelm Ohlendorf, Garbsen; Wilhelm Kaupmann, Hanover; Ulrich Kuhl, Gehrden; Gerd Buschmann; Stephen J. Magda, both of Hanover, all of Fed. Rep. of Germany

[73] Assignee: Kali-Chemie Pharma GmbH, Hanover, Fed. Rep. of Germany

[*] Notice: The portion of the term of this patent subsequent to Feb. 7, 2006 has been disclaimed.

[21] Appl. No.: 123,201

[22] Filed: Nov. 20, 1987

Related U.S. Application Data

[63] Continuation of Ser. No. 879,624, Jun. 27, 1986, abandoned, which is a continuation of Ser. No. 772,678, Sep. 5, 1985, abandoned, which is a continuation of Ser. No. 577,711, Feb. 7, 1984, abandoned.

[51] Int. Cl.$^4$ ............... A61K 31/405; C07D 209/42
[52] U.S. Cl. ............... 514/418; 514/228.2; 514/235.2; 514/323; 514/419; 544/62; 544/144; 546/201; 548/454; 548/467; 548/484; 548/492
[58] Field of Search ........... 514/228.2, 235.2, 323, 514/418, 419; 544/62, 144; 546/201; 548/454, 467, 484, 492

[56] References Cited

U.S. PATENT DOCUMENTS 4,059,583 11/1977 McComsey .................. 548/484

FOREIGN PATENT DOCUMENTS 71935 2/1983 European Pat. Off. ........ 548/484
1527M 10/1962 France ........................ 548/484

OTHER PUBLICATIONS

Ariens, E. J., *Drug Design*, (1971: Academic Press, N.Y.), pp. 10–11.
Burger, A., *Medicinal Chemistry*, 3rd ed., (1970: Wiley-Interscience, N.Y.), pp. 71 and 55.
Burger, A., *Medicinal Chemistry*, Part I, 4th ed., (1980: Wiley-Interscience, N.Y.), p. 175.

*Primary Examiner*—Donald G. Daus
*Assistant Examiner*—Mark W. Noel
*Attorney, Agent, or Firm*—Foley & Lardner, Schwartz, Jeffery, Schwaab, Mack, Blumenthal & Evans

[57] ABSTRACT

Novel 1-phenyl-2-aminocarbonylindole compounds are disclosed having the general formula I

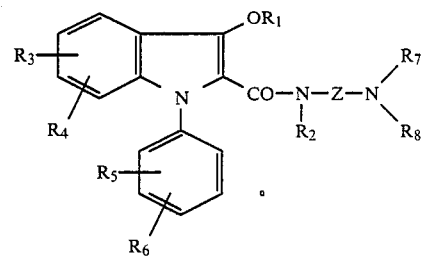

wherein $R_1$ is an aliphatic or aromatic acyl group or an optionally substituted benzyl group; $R_2$ is hydrogen or a lower alkyl radical; $R_3$ is a hydrogen, a halogen, a lower alkyl radical, or a lower alkoxy radical; $R_4$ is hydrogen, a halogen, a lower alkyl radical, or a lower alkoxy radical; $R_5$ has the significance given $R_3$; $R_6$ has the significance given for $R_4$, or $R_6$ is nitro or trifluoromethyl; $R_7$ and $R_8$ each represent hydrogen or a lower alkyl radical, or together with a nitrogen atom form a heterocyclic group; and Z signifies an alkylene chain optionally substituted by hydroxy or acyloxy. The compounds have pharmacological, in particular antiarrhythmic, properties.

18 Claims, No Drawings

1-PHENYL-2-AMINOCARBONYLINDOLE COMPOUNDS, PREPARATION THEREOF AND PHARMACEUTICAL COMPOSITIONS CONTAINING THEM

BACKGROUND OF THE INVENTION

This application is a continuation of application Ser. No. 879,624, filed June 27, 1986, which is a continuation of Ser. No. 772,678, filed Sept. 5, 1985, which is a continuation of Ser. No. 577,711 filed Feb. 7, 1984, all now abandoned.

The present invention relates to novel 3-acyloxy-and 3-benzyloxy-1-phenyl-2-alkylaminocarbonylindole compounds and salts thereof and pharmaceutical compositions containing these compounds.

U.S. Pat. No. 3,573,325 describes 2- carboxamidoindole compounds having antiemetic properties and a depressant action on the central nervous system. U.S. Pat. No. 3,198,807 describes 2-carboxamidoindole compounds which also have antiemetic properties and, in addition, local anesthetic and antifibrillatory properties.

SUMMARY OF THE INVENTION

It is an object of the invention to develop novel 1-phenyl-2-aminocarbonylindole compounds with valuable pharmaceutical properties.

It has been discovered that the new 1-phenol-2-aminocarbonylindole compounds substituted in position 3 by acyloxy or benzyloxy radicals, possess valuable pharmacological effects, especially antiarrhythmic activity, and exhibit an advantageous action profile with a good therapeutical range and low toxicity. On the basis of these actions, the new compounds are suitable as pharmaceuticals, in particular for the treatment of disorders in cardiac rhythm.

DETAILED DESCRIPTION OF PREFERRED EMBODIMENTS

The present invention thus relates to novel 1- phenyl-2-aminocarbonylindole compounds of general formula I

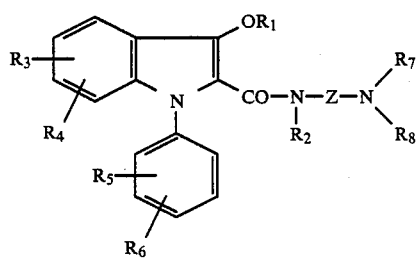

wherein $R_1$ represents (i) an alkanoyl group with 2 to 12 carbon atoms, which optionally may be substituted by a carboxyl or lower alkoxycarbonyl group or a lower alkoxy or benzyloxy; or (ii) a group a having the formula

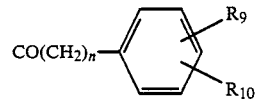

wherein n is 0, 1, 2 or 3, and $R_9$ and $R_{10}$ represent independently of each other a hydrogen or halogen atom, a lower alkyl or lower alkoxy radical or, if they are bonded to 2 adjacent carbon atoms, together form a methylenedioxy radical, or, if n is equal 0 and $R_9$ represents hydrogen, $R_{10}$ may signify nitro or trifluoromethyl, or (iii) benzyl, again optionally substituted by 1 or 2 substituents of the group of lower alkyls, lower alkoxyls, nitro and halogens.

$R_2$ signifies hydrogen of a lower alkyl radical, $R_3$ signifies hydrogen, a lower alkyl or lower alkoxy radical, $R_4$ signifies hydrogen, a halogen, a lower alkyl or lower alkoxy radical, $R_5$ signifies hydrogen, a lower alkyl, a halogen or lower alkoxy radical, $R_6$ signifies hydrogen, a lower alkyl, lower alkoxy radical, a halogen, or, if $R_5$ is hydrogen, also nitro or trifluoromethyl, $R_7$ is a hydrogen or a lower alkyl radical, $R_8$ is a hydrogen or a lower alkyl radical, or $R_7$ and $R_8$ together with the nitrogen atom to which they are bonded may form a heterocyclic group b,

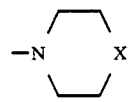

wherein X represents a bond, $-CH_2$, $-C_2H_4-$, O or S, Z signifies an alkylene chain with 2 to 5 carbon atoms, which again may be substituted on a carbon not bonded to nitrogen, by hydroxy or a $R'_1O$ group, wherein $R'_1$ has the meaning given for $R_1$, with the exception of optionally substituted benzyl, and to the acid addition salts of the Formula (I) compounds.

If in the compounds of Formula I the substituents $R_3$ to $R_6$ of the phenyl rings contain a lower alkyl group, this may be straight or branched and in particular may contain 1 to 4 carbon atoms. Thus, specifically methyl, ethyl, n-propyl, isopropyl, n-propyl or tert-butyl, preferably methyl or ethyl radicals, are suitable. In particular, in the case of disubstitutions on the phenyl rings, the alkyl-containing substituents preferably are methyl or methoxy radicals.

Possible halogen substituents in the phenyl rings include particularly fluorine, chlorine or bromine, preferably chlorine or bromine.

The substituents $R_3$ and $R_4$ preferably represent hydrogen or halogen atoms. The substituents $R_5$ and $R_6$ preferably are hydrogen, a halogen atom or a lower alkyl radical.

The substituent $R_2$ in particular signifies hydrogen. If $R_2$ is a lower alkyl radical, the latter contains 1 to 4, in particular 1 to 2 carbon atoms.

If $R_7$ and/or $R_8$ signify a lower alkyl radical, the latter may be straight or branched and may contain in particular 1 to 4 carbon atoms. Especially, the methyl, ethyl, propyl and butyl radicals are suitable as the alkyl groups. Specifically, the $NR_7R_8$ group represents a preferably straight dialkylamino group, for example the diethylamino radical.

Z represents an alkyl chain with 2 to 5 carbon atoms, preferably a straight alkyl chain with 2 to 4 carbon atoms. If Z signifies an alkyl chain substituted by a hydroxy radical or $R'_1O$, it preferably is a 2-hydroxypropylene or a 2-$R'_1O$ propylene chain.

If an acyl group or a substituted benzyl group $R_1$ carries substituents containing a lower alkyl radical, the latter contain in particular 1 to 4 carbon atoms and represent preferably methyl or ethyl.

An $R_1$ acyl group represents the acid residue of an aliphatic or aromatic carboxylic acid. As the aliphatic carboxylic acids, lower monocarboxylic acids with preferably 1 to 4 carbon atoms in the alkyl chain, such as acetic acid, propionic acid or propane- or butane-carboxylic acids, are suitable. Further, substituted lower carboxylic acids with preferably 1 to 4 carbon atoms in the alkyl chain, for example, lower dicarboxylic acids, such as succinic acid or the lower monoalkylesters thereof, and moncarboxylic acids substituted with lower alkoxy radicals, in particular methoxy or benzyloxy radicals, are suitable. Potentially substituted straight or branched chain aliphatic carboxylic acids with up to 11, for example 5 to 11 carbon atoms in the alkyl chain, for example, capronic acid, caprylic acid or laurinic acid, are also suitable.

Optionally substituted phenylalkylcarboxylic acids with up to 3 carbon atoms in the alkyl chain and in particular optionally substituted benzoic acids, are suitable as the aromatic acids.

The following may be cited as suitable $R_1$ acid residues: acetyl, propionyl, isobutyryl, valeroyl, pivaloyl, isovaleroyl, dodecanoyl, benzoyl, chlorobenzoyl, nitrobenzoyl, methylbenzoyl, methoxybenzoyl, phenylacetyl, hydroxycarbonylethylcarbonyl, methoxycarbonylethylcarbonyl Thus, the compounds according to the invention include among others:

2-[3-(N,N-diethylamino)-2-hydroxypropylaminocarbonyl]-3-pivaloyloxy-1-phenylindole,
2-[3-(N,N-diethylamino)-2-propionyloxypropylaminocarbonyl]-3-propionyloxy-1-phenylindole,
2-[3-(N,N-diethylamino)-2-hydroxypropylaminocarbonyl]-3-isobutyryloxy-1-phenylindole,
2-[3-(N,N-diethylamino)-2-hydroxypropylaminocarbonyl]-3-dodecanoyloxy-1-phenylindole,
2-[3-(N,N-diethylamino)-2-hydroxypropylaminocarbonyl]-3-benzoyloxy-1-phenylindole,
2-[3-(N,N-diethylamino)-2-hydroxypropylaminocarbonyl]-3-o-chlorobenzoyloxy-1-phenylindole,
2-[3-(N,N-diethylamino)-2-hydroxypropylaminocarbonyl]-3-m-chlorobenzoyloxy-1-phenylindole,
2-[3-(N,N-diethylamino)-2-hydroxypropylaminocarbonyl]-3-p-chlorobenzoyloxy-1-phenylindole,
2-[3-(N,N-diethylamino-2-hydroxypropylaminocarbonyl]-3-p-nitrobenzoyloxy-1-phenylindole,
2-[3-(N,N-diethylamino)-2-hydroxypropylaminocarbonyl]-3-p-methylbenzoyloxy-1-phenylindole,
2-[3-(N,N-diethylamino)-2-hydroxypropylaminocarbonyl]-3-m,p-dimethoxybenzoyloxy-1-phenylindole,
2-[3-N,N-diethylamino)-2-hydroxypropylaminocarbonyl]-3-phenylacetoxy-1-phenylindole,
2-[3-(N,N-diethylamino)-2-hydroxypropylaminocarbonyl]-3-benzyloxy-1-phenylindole,,
2-[3-(N,N-diethylamino)-2 -hydroxypropylaminocarbonyl]-3-methoxycarbonylmethylcarbonyloxy-1-phenylindole,
2-[3-(N,N-diethylamino)-2-hydroxypropylaminocarbonyl]-3-hydroxycarbonylethylcarbonyloxy-1-phenylindole,
2-[3-(N,N-diethylamino)-2-hydroxypropylaminocarbonyl]-3-methoxycarbonylethylcarbonyloxy-1-phenylindole,
2-[3-(N,N-diethylamino)-2-hydroxypropylaminocarbonyl]-3-benzoyloxy-1-(4-chlorophenyl)-indole,
2-[3-(N,N-diethylamino)-2-hydroxypropylaminocarbonyl]-3-methoxyacetoxy-1-phenylindole,
2-[3-(N,N-diethylamino)-2-benzoyloxypropylaminocarbonyl]-3-benzoyloxy-1-(4-chlorophenyl)-indole,
2-[3-(N,N-diethylamino)-2-acetoxypropylaminocarbonyl]-3-acetoxy-1-phenylindole,
2-[3-(N,N-diethylamino)-2-benzoyloxypropylaminocarbonyl]-3-benzoyloxy-1-phenylidole,
2-[3-(N,N-diethylamino)-2-hydroxypropylaminocarbonyl]-3-pivaloyloxy-1-phenyl-5-bromoindole,
2-[3-(N,N-diethylamino)-2-hydroxypropylaminocarbonyl]-3-pivaloyloxy-1-phenyl-4-chloroindole,
2-[3-(N,N-diethylamino)-2-hydroxypropylaminocarbonyl]-3-pivaloyloxy-1-(4-methoxyphenyl)-indole,
2-[3-(N,N-diethylamino)-2-hydroxypropylaminocarbonyl]-3-pivaloyloxy-1-(4-fluorophenyl)-indole,
2-[3-(N,N-diethylamino)-2-hydroxypropylaminocarbonyl]-3-pivaloyloxy-1-(4-methoxyphenyl)-indole,
2-[3-(N,N-diethylamino)-2-propionyloxypropylaminocarbonyl]-3-propionyloxy-1-phenyl-5-bromoindole,
2-[3-(N,N-diethylamino)-2-hydroxypropylaminocarbonyl]-3-benzoyloxy-1-phenyl-4-chloroindole,
2-[3-(N,N-diethylamino)-2-hydroxypropylaminocarbonyl]-3-benzoyloxy-1-(4-fluorophenyl)-indole,
2-[3-(N,N-diethylamino)-2-hydroxypropylaminocarbonyl]-3-pivaloyloxy-1-(4-chlorophenyl)-indole,
2-[3-(N,N-dimethylamino)-2-hydroxypropylaminocarbonyl]-3-benzoyloxy-1-(4-methoxyphenyl)-indole,
2-(3-pyrrolidino-2-hydroxypropylaminocarbonyl)-3-pivaloyloxy-1-phenylindole,
2-(3-pyrrolidino-2-benzoyloxypropylaminocarbonyl)-3-benzoyloxy-1-phenylindole,
2-(3-morpholino-2-hydroxypropylaminocarbonyl)-3-pivaloyl-1-phenylindole,
2-(3-morpholino-2-hydroxypropylaminocarbonyl)-3-benzoyloxy-1-phenylindole,
2-[2-(N,N-dimethylamino)-ethylaminocarbonyl]-3-acetoxy-1-phenylindole,
2-[3-(N,N-diethylamino)-propylaminocarbonyl]-3-acetoxy-1-phenylindole,
2-[4-(N,N-diethylamino)-butylaminocarbonyl]-3-acetoxy-1-phenylindole,
2-[2-(N,N-dimethylamino)-ethylaminocarbonyl]-3-propionyl-1-phenylindole,
2-[3-(N,N-diethylamino)-propylaminocarbonyl]-3-propionyloxy-1-phenylindole,
2-[4-(N,N-diethylamino)-butylaminocarbonyl]-3-propionyloxy-1-phenylindole, 2-[2-(N,N-dimethylamino)-ethylaminocarbonyl]-3-benzoyloxy-1-phenylindole,
2-[3-(N,N-diethylamino)-propylaminocarbonyl]-3-benzoyloxy-1-phenylindole,
2-[4-(N,N-diethylamino)-butylaminocarbonyl]-3-benzoyloxy-1-phenylindole,
2-[2-(N,N-dimethylamino)-ethylaminocarbonyl]-3-pivaloyloxy-1-(2,3-dimethylphenyl)-indole,
2-[3-(N,N-dimethylamino)-propylaminocarbonyl]-3-pivaloyloxy-1-(4-chlorophenyl)-indole,
2-[2-(N,N-dimethylamino)-ethylaminocarbonyl]-3-pivaloyloxy-1-(4-chlorophenyl)-indole,
2-[2-(N,N-dimethylamino)-ethylaminocarbonyl]-3-pivaloyloxy-1-phenyl-5-bromoindole, The new 3-acyloxy-1-phenyl-2-aminocarbonylindole compounds of Formula Ia

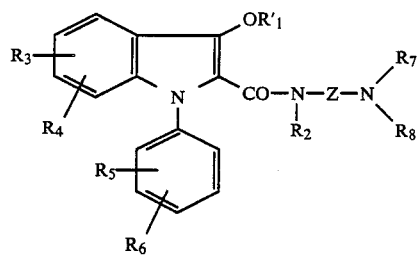

wherein $R'_1$, $R_2$, $R_3$, $R_4$, $R_5$, $R_6$, $R_7$, $R_8$ and Z have the above defined significance, and the acid addition salts thereof, may be obtained by using conventional techniques to acylate compounds of the general formula II

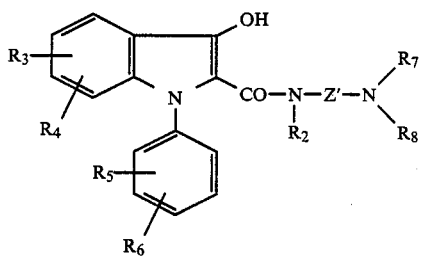

wherein $R_2$, $R_3$, $R_4$, $R_5$, $R_6$, $R_7$ and $R_8$ are defined as above and Z' is an alkylene chain with 2 to 5 carbon atoms, optionally substituted at a carbon atom not bonded to nitrogen with a hydroxy radical, by means of an acid derivative of the general formula III $$R_1'-X \qquad \text{III}$$

wherein $R'_1$ has the above-defined significance and X is a reactive group, or, if $R'_1$ contains a free carboxyl group, optionally a cyclic anhydride of an acid $R'_1OH$. Free compounds of Formula Ia may further by converted into their acid addition salts or, conversely, the acid addition salts into the free compounds of Formula Ia.

The reaction of acid derivatives of Formula III or of cyclic anhydrides with the hydroxy compounds of Formula II may be effected by methods conventionally applied to the formation of esters by acylation. Suitable reactive derivatives are in particular acid halides, preferably chlorides, esters, and anydrides or mixed anhydrides of the $R'_1OH$ acids, for example compounds of Formula III, wherein the reactive group X is (a) a halogen, in particular chlorine or bromine, (b) an $OR'_1$, wherein $R'_1$ has the above-defined significance, or (c) an O—CO—W group, wherein W is a lower alkyl radical or a lower alkoxy radical. Acylation may be effected in a solvent inert under the conditions of the reaction, at temperatures between room temperature and the boiling point of the solvent. Suitable solvents are halogenated hydrocarbons such as methylene chloride or chloroform, aromatic hydrocarbons such as benzene, toluene, xylene or chlorobenzene, cyclic ethers, such a tetrahydrofuran or dioxane, and dimethylformamide, or mixtures thereof.

The acylation is appropriately performed in the presence of an acid binding reagent. Suitable acid binding agents are inorganic bases, in particular alkali metal carbonates and hydroxides, such as potassium carbonate or potassium hydroxide, or organic bases, in particular tertiary lower alkylamines and pyridines, such as triethylamine or 4-dimethylaminopyridine.

If the initial compounds contain, in addition to the hydroxy group in position 3 to be esterified, a further free hydroxy group in the side chain link Z', under the aforementioned conditions of acylation, the latter takes place preferentially at the enolic hydroxy group in position 3. Depending on the amount of the acid derivative added and the duration of the reaction, the hydroxy group in the side chain may, however, also become acylated to a $R'_1O$ group. Mixtures of mono-and diacylated compounds of Formula Ia which may result may be separated by known methods, for example, chromatography.

For the preparation of compounds of Formula Ia containing a free hydroxy group in the side chain link Z, in the corresponding initial compounds of Formula II the free hydroxy group in the Z' link may be provided if so desired, prior to the reaction in a known manner with a protective group, which subsequently may easily be split off, under conditions in which the ester group in position 3 is not attacked. For example, easily cleavable carbonates, such as benzyl carbonate, are suitable for the protection of a secondary aliphatic hydroxy group.

The new compounds of Formula Ib

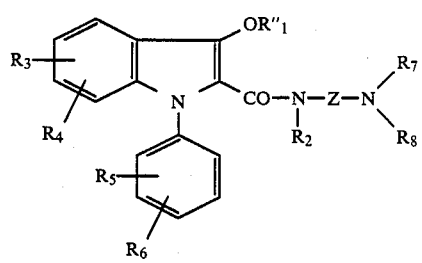

wherein $R_2$, $R_3$, $R_4$, $R_5$, $R_6$, $R_7$, $R_8$ and Z have the above-defined significance and $R_1''$ is benzyl, which optionally may be substituted by 1 or 2 substituents from the group of lower alkyl or lower alkoxy radicals, or by a halogen atom, and the acid solution salts thereof, may be obtained by reacting compounds of Formula Va

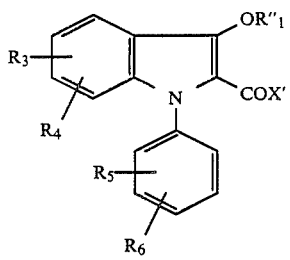

wherein $R_3$, $R_4$, $R_5$, $R_6$ and $R_1''$ have the above-defined significance and $X'$ is a reactive group, with a compound of Formula VI

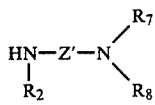

wherein $R_2$, $R_7$, $R_8$ and $Z'$ have the aforementioned meaning. If so desired, in the compounds of Formula Ib thereby synthesized, wherein Z contains a free hydroxy group, the latter may be acylated in a known manner, and/or optionally free compounds of Formula Ib may be converted into their acid addition salts or vice versa.

The reaction of the acid derivatives of Formula Va with amines of Formula VI may be effected by conventional methods used for the formation of amide groups by amino acylation. Suitable reactive derivatives are in particular acid halides, preferably chlorides, esters and mixed anhydrides, for example compounds of Formula Va, wherein the reactive group $X'$ is a halogen, especially chlorine or bromine, a lower alkoxy radical, especially an alkoxy radical with 1 to 4 carbon atoms, or an O—CO—W group, wherein W is a lower alkyl or lower alkoxy radical. Further acid derivatives suitable for amide formation are known from peptide chemistry; they may be formed by the reaction of the corresponding acids with known coupling reagents (see, for example, Mukayama, ANGEW. CHEMIE 91: 789–812). Aminoacylation may be effected in a solvent that is inert under the conditions of the reaction, at temperatures between room temperature and the boiling point of the solvent. Suitable solvents are halogenated hydrocarbons, such as methylene chloride of chloroform, aromatic hydrocarbons such as benzene, toluene, xylene or chlorobenzene, cyclic ethers such as tetrahydrofuran or dioxane, and dimethylformamide, or mixtures thereof.

Aminoacylation may be performed optionally, especially when an acid halide or anhydride of Formula Va is used, in the presence of an acid binding reagent. Suitable acid binding agents are inorganic bases, in particular alkali metal carbonates and hydroxides, such as sodium or potassium carbonate or potassium hydroxide, or organic bases, in particular tertiary lower alkylamines and pyridines, such as triethylamine, pyridine or 4-dimethylaminopyridine. In place of a foreign base, an excess of the amino of Formula VI may also be used. Organic bases used in excess may serve simultaneously as solvents.

The acylation of a free OH group in the side chain of compounds of Formula Ib may be effected in a known manner, for example, by the methods given above for the acylation of compounds of Formula II to compounds of Formula Ia.

By the reaction sequences described herein, compounds of Formula I, wherein Z contains a hydroxy or an acyloxy group, are obtained in the form of their racemates. The racemic mixtures and the optically active forms of these compounds are included in the scope of the present invention. The optically active compounds may be separated into their optically active antipodes in a known manner by means of conversion with suitable, optically active acids, such as for example tartaric acid, O,O'-dibenzoyl-tartaric acid, mandelic acid, di-O-isopropylidene-2-oxo-L-gulonic acid, and subsequent fractionating crystallization of the salts thereby obtained.

The separation into optically active compounds may be effected, if so desired, in a suitable intermediate stage, for example, the compounds of Formula II.

The compounds of Formula I may be isolated using conventional methods from the reaction mixture and purified. Acid addition salts may be converted into the free bases in a conventional manner, and these can be converted into pharmacologically compatible acid addition salts.

Suitable, pharmacologically acceptable acid addition salts of the compounds of Formula I, are for example, their salts with hydrochloric acid, hydrobromic acid, sulfuric acid, phosphoric acid, methanesulfonic acid, ethanesulfonic acid, cyclohexylaminosulfonic acid, amidosulfonic acid, acetic acid, lactic acid, tartaric acid, phenylacetic acid, and mandelic acid. If the residue $R_1$ of the compounds of Formula I contains an additional free COOH group, the compounds may also form internal salts.

The starting compounds of Formula II may be obtained by liberating in a known manner the hydroxy group in the 3 position from compounds of Formula IV

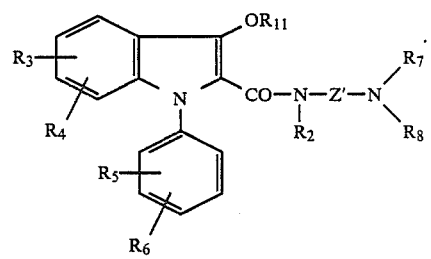

wherein $R_2$, $R_3$, $R_4$, $R_5$, $R_6$, $R_7$, $R_8$ and $Z'$ have the above-defined significance and $R_{11}$ is methyl or a hydrogenolytically cleavable group, for example, an optionally substituted benzyl group.

The cleavage of the $OR_{11}$ group may be effected by known methods used to split ethers. For example, benzyl ethers may be cleaved hydrogenolytically.

Compounds of Formula II may further be obtained by reacting compounds of Formula X

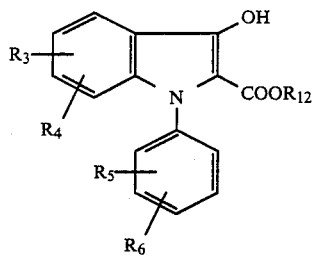

wherein $R_3$, $R_4$, $R_5$ and $R_6$ have the above-defined significance and $R_{12}$ has a lower alkyl radical, with compounds of Formula VI. The reaction may be effected by known methods for esteraminolysis, for example, by the methods among others given above for the reaction of compounds of Formula Va with compounds of Formula VI.

The initial compounds of Formula IV may be prepared in a known manner by reacting compounds of Formula V

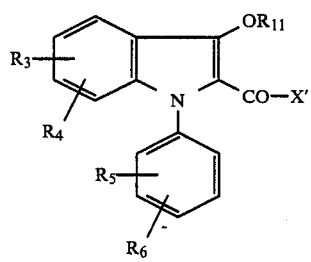

wherein $R_3$, $R_4$, $R_5$, $R_6$, $R_{11}$ and X' have the above-defined significance, with a compound of Formula VI. The reaction may be conventionally effected by the methods given above for the reaction of compounds of Formula Va with compounds of Formula VI.

Compounds of Formula Vb

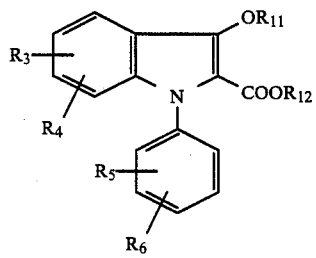

wherein $R_3$, $R_4$, $R_5$, $R_6$, $R_{11}$ have the above-defined significance, may be obtained in a known manner by:

(a') cyclizing compounds of Formula VII

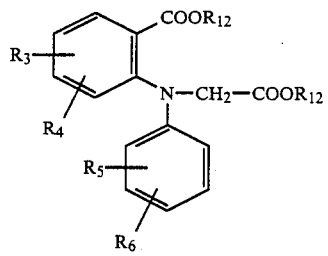

wherein $R_3$, $R_4$, $R_5$, $R_6$ and $R_{12}$ have the above-defined significance, in a known manner to compounds of Formula X and converting these in a known manner, for example by methods used in etherization, into compounds of Formula Vb; or (b') reacting compounds of Formula VIII

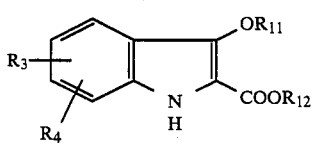

wherein $R_3$, $R_4$, $R_{11}$ have the above-defined significance, with compounds of Formula IX

wherein $R_5$ and $R_6$ have the above-defined significance and Hal means halogen.

The compounds of Formula Vb may be subsequently hydrolyzed in a known manner to the corresponding acids and the latter converted by conventional means into further reactive acid derivatives. The conversion of the free acids to reactive acid derivatives is again effected in a known manner. Thus, acid halides of Formula V may be obtained by the reaction of acids with an inorganic acid halide. Mixed acid anhydrides may be obtained, for example, by reacting alkaline metal salts of the acids with a corresponding organic acid chloride in the presence of a tertiary organic base.

The cyclization of the compounds of Formula VII according to process variant (a') is effected conveniently in a solvent that is inert under the conditions of the reaction in the presence of a strong base at an elevated temperature, for example, at temperatures between 50° and 150° C. Suitable strong bases are for example lower alkali metal alcoholates, such as sodium ethylate. Suitable inert solvents are, for example, the corresponding lower alcohols, aromatic hydrocarbons, such as toluene or xylene, or mixtures of such solvents. In the reaction the compound of Formula X is obtained in the form of its alkali metal salt and may be released during processing by acidifying the reaction mixture.

The initial compounds of Formula VII required for the process variant (a') may be obtained in a manner known to the art beginning with phenylglycine compounds which are represented by Formula XI

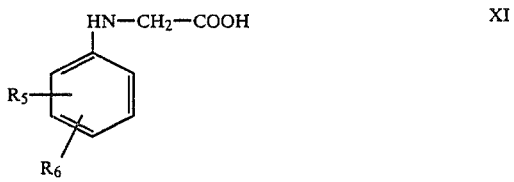

wherein $R_5$ and $R_6$ have the above-defined significance, and which may be obtained by the reaction of the corresponding anilines with chloracetic acid, and o-chlorobenzoic acids of Formula XII

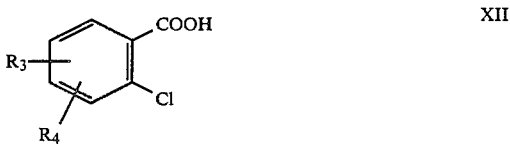

wherein $R_3$ and $R_4$ have the above-defined significance. The alkali metal salts, in particular potassium salts, of the acids of Formula XI are converted with alkali metal salts, in particular potassium salts, of the acids of Formula XII at an elevated temperature, for example, at temperatures between 100° and 150° C., in the presence of an inorganic base, for example, potassium carbonate, and a copper catalyst, such as copper powder, in a polar solvent, preferably water or a mixture of water and an organic solvent miscible with water, to compounds of Formula XIII

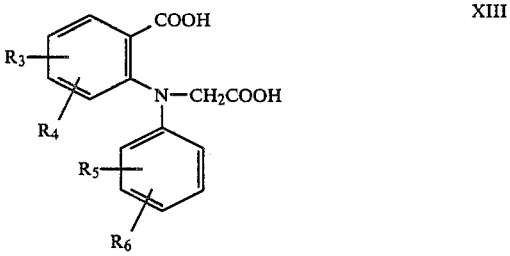

wherein $R_3$, $R_4$, $R_5$ and $R_6$ have the above-defined significance, and the latter are subsequently esterified in a conventional manner to compounds of Formula VII, such as by reaction with an alcohol $R_{12}$ in the presence of sulfuric acid at an elevated temperature, for example the boiling temperature of the reaction mixture.

The above-described process variant (a') is particularly suitable for the production of compounds Vb, in which $R_3$ and $R_4$ stand for hydrogen or for substituents which are not capable of reaction with phenylglycine. If the compound of Formula XIII contains further substituents capable of reaction with phenylglycine, in the course of this reaction multiply substituted by-products may be formed in the reaction mixture in addition to the compound of Formula XIII. The reaction product desired may be separated chromatographically from any potential by-product.

Compounds of Formula VIII may be reacted with compounds of Formula IX according to the process variant (b') in a manner known to the art. Conveniently, the compounds of Formula VIII are reacted in the form of their alkali metal salts, for example, their sodium or lithium salts, with compounds of Formula IX in a solvent that is inert under the conditions of the reaction, at temperatures between approximately 100° and 170° C. Suitable solvents are inert organic solvents boiling within the temperature range indicated, preferably dimethylformamide. It is appropriate to conduct the reaction in the presence of a copper catalyst, for example, copper powder or copper-I or copper-II halides. The alkali metal salts of the compounds of Formula VIII may be prepared by reaction with a strong base, for example, an alkaline metal alcoholate or hydride or hydroxide, in situ if so desired.

The initial compounds of Formula VIII required for the process variant (b') may be prepared in a known manner beginning with anthranilic acid esters of Formula XIV

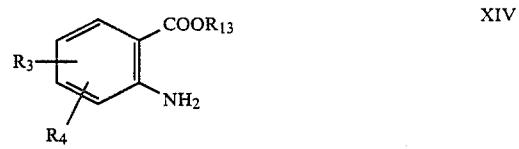

wherein $R_3$ and $R_4$ have the above-defined significance and $R_{13}$ is a lower alkyl radical, by initially converting the esters with chloracetic acid or a lower alkyl ester of chloracetic acid, in a conventional manner to compounds of Formula XV

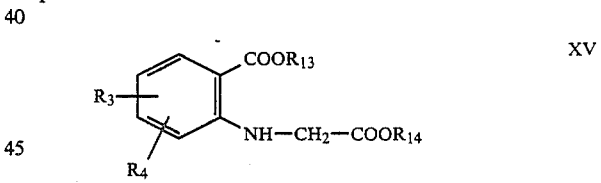

wherein $R_3$, $R_4$ and $R_{13}$ have the above-defined significance and $R_{14}$ is hydrogen or a lower alkyl radical. If $R_{14}$ is a hydrogen atom, this acid is esterified in a known manner with a $R_{12}OH$ alcohol, wherein $R_{12}$ has the above-defined significance, and the diesters obtained are cyclized, in a manner known to the art, to compounds of Formula XVI

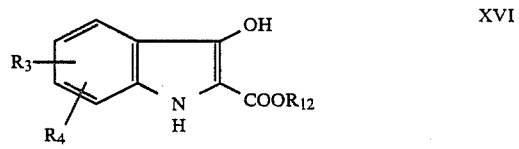

wherein $R_3$, $R_4$ and $R_{12}$ have the above-defined meaning. The resulting compounds are converted by known means to compounds of Formula VIII, by etherifying the hydroxy group. The cyclization of the esters of Formula XV may be effected, for example, under the above-described conditions for the cyclization of the esters of Formula VII.

The process variant (b') is suitable in particular for the preparation of compounds of Formula V6, wherein $R_5$ and $R_6$ represent hydrogen or substituents not capable of reaction with the alkaline metal salts of compounds of Formula XIII.

The compounds of Formula I and the pharmacologically acceptable acid addition salts thereof exhibit interesting pharmacological properties and in particular have a cardiac rhythmizing action. The novel compounds are distinguished by good efficacy and a high physiological tolerance. Thus, the new compounds have a satisfactory antiarrhythmic effect even in low doses. Furthermore, any undesirable negative effect on the contractility of the heart is extremely low. Thus, the compounds are characterized by a particularly advantageous relationship between antiarrhythmic action and the effects extending the refractory period of the heart, respectively, and negative inotropic side effects, and they possess a wide therapeutic range.

The doses to be applied naturally vary as a function of the type of substance used, the mode of application, and the condition to be treated. In general, however, satisfactory results are obtained in animal experiments with doses of 0.1 to 100 mg/kg of body weight.

The antiarrhythmic effects of the compounds may be demonstrated by standard pharmacological test methods.

A favorable relationship between the action (FRZ) extending the functional refractory time and the effect (force) reducing the contracting force of the compounds may be demonstrated using the isolated left auricle of female guinea pigs with body weights of 300 to 400 g, according to the double stimulation method of Govier [J. PHARMACOL. EXP. THER. 148: 100–105 (1965)]. In the table below, the concentrations are given in $\mu$mole/l, whereby in 18 minutes after the application the functional refractory time is extended by 125%; the concentration whereby the contractile force is reduced to 75% of the individual value; and further the quotient of these concentrations, representing an indication of the therapeutic range of the compounds.

| Example No. | Isolated guinea pig auricle | | Force FRZ |
|---|---|---|---|
| | Force micro- [mole/l] | FRZ micro- [mole/l] | |
| 4 | 4.2 | 3.0 | 1.4 |
| 3 | 6.2 | 2.8 | 2.2 |
| 21 | 1.8 | 0.73 | 2.5 |

Similarly, the compounds exhibit with rats, in the test method according to Raschak [ARZNEIMITTEL-FORSCH. 25: 639–641 (1975)], an inhibiting effect on cardiac rhythm disturbances.

Based on the effects described above, the compounds of Formula I and the pharmacologically acceptable acid addition salts thereof are suitable for the treatment of cardiac rhythm disturbances.

The substances of Formula I also exhibit antithrombotic properties.

As medicaments, the compounds of Formula I and their physiologically tolerable acid addition salts along with the usual pharmaceutical auxiliary substances may be contained in galenic preparations, for example, tablets, capsules, suppositories, or solutions. These galenic preparations may be prepared by known methods, using conventional solid carrier substances, such as lactose starch or talcum, or liquid diluting agents, such as water, fatty oils or liquid paraffins.

The following examples are intended to illustrate the preparation of the new compounds of Formula I in more detail, but do not limit the scope of the invention to any extent.

EXAMPLE 1

2-[3-(N,N-diethylamino)propylaminocarbonyl]-3-acetoxy-1-phenylindole (A) 475 g of chloracetic acid (5 moles) are heated with 930 g aniline (10 moles) in 2 l water for 1.5 h to 100° C. After cooling, the N-phenylglycine formed is suctioned off and washed with water. Yield is 468 g (=62% with respect to the chloracetic acid).

(B) 468 g N-phenylglycine are dissolved with heating in 1.3 l methanol. The solution is reacted under cooling with 205 g potassium hydroxide in 450 ml of methanol. After cooling, the precipitated potassium salt of N-phenylglycine is suctioned off. Yield is 392 g=67%.

(C) 468 g of o-chlorobenzoic acid are dissolved with heating in 1.5 l isopropanol. The solution is reacted under cooling with a solution of 198 g of potassium hydroxide in 200 ml of methanol. After cooling, the precipitated potassium salt of the o-chlorobenzoic acid is suctioned off. Yield is 394 g=67.4%.

(D) 750 g of the potassium salt of N-phenylglycine are heated with 808 g of the potassium salt of o-chlorobenzoic acid, 268 g of potassium carbonate and 1.5 g of copper powder in 385 ml of water for 5 h to 120° to 125° C. (internal temperature). Following the dissolution of the reaction mixture in water, the solution is acidified with hydrochloric acid and the N-diphenylglycine-o-carboxylic acid suctioned off. Yield 675 g=62.7%.

(E) 675 g of N-diphenylglycine-o-carboxylic acid are heated with 2.5 l of methanol and 500 ml of sulfuric acid for 5 h to boiling. The methanol is partially evaporated, the reaction mixture subsequently poured into water and extracted with methylene chloride. The methylene chloride phase is extracted by shaking with a solution of sodium carbonate, dried and evaporated, whereby the raw N-diphenylglycine-o-carboxylic acid dimethylester is obtained as the residue. Yield is 614 g of the raw product=82.4%.

(F) 47.1 g of sodium are dissolved in 500 ml methanol and the solution diluted with 500 ml of toluene. The mixture is heated to boiling and mixed under a weak reflux with a solution of 614 g of N-diphenylglycine-o-carboxylic acid dimethylester in 1.5 l of toluene. After a further 30 min boiling, the reaction mixture is cooled, poured into 1 l of water of acidified with 250 ml of hydrochloric acid. The N-phenylindoxylic acid methylester precipitated is suctioned off. Yield is 464 g=84.8%.

(G) 140 g of N-phenylindoxylic acid methylester are heated in 600 ml of acetone with 69 ml of dimethylsulfate and 71 g of potassium carbonate for 4 h with agitation to the boiling point. The reaction mixture is poured into water and the N-phenyl-3-methoxyindole-2-carboxylic acid methylester formed is suctioned off and dissolved in 450 ml of methanol. The solution is diluted with 42 g of sodium hydroxide in 50 ml of water and heated to boiling for 30 min. The reaction mixture is dissolved in water, the aqueous solution acidified with hydrochloric acid and the N-phenyl-3-methoxyindole-2-carboxylic acid suctioned off. Yield is 127 g=90.7%.

(H) 92 g of N-phenyl-3-methoxyindole-2-carboxylic acid are dissolved in 920 ml of ether and 30.3 g of pyridine. The solution is added drop-wise to a solution of 28.3 ml of thionyl chloride in 160 ml of ether under agitation and cooling with ice. The mixture is agitated for 1 h at room temperature and the pyridine salts thereby precipitated is suctioned off.

The ether solution of N-phenyl-3-methoxyindole-2-carboxylic acid chloride obtained is added drop-wise to a solution of 550 g of 1-amino-3-diethylaminopropane and 40 g of triethylamine in 70 ml of methylene chloride under cooling with ice. The reaction mixture is agitated for 1 h at room temperature and subsequently extracted with dilute hydrochloric acid. The hydrochloric acid extract is made alkaline by the addition of a sodium hydroxide solution and extracted with ether. The ether solution is washed with water, dried over sodium sulfate, and evaporated. 2-[3-(N,N-diethylamino)-propylaminocarbonyl]-3-methoxy-1-phenylindole remains as an oily base. The latter is dissolved in isopropanol and converted into the hydrochloride thereof. Melting point is 125°-137° C.

(I) 2.1 g of 2-[3-(N,N-diethylamino)propylaminocarbonyl]-3-methoxy-1-phenylindole hydrochloride are dissolved in 5 ml of methanol and mixed with 2.5 ml concentrated hydrochloric acid. The reaction mixture is boiled for 3 h under reflux and subsequently evaporated under vacuum. 1.66 g (82% of theoretical) 2-[3-(N,N-diethylamino)propylaminocarbonyl]-3-hydroxy-1-phenylindole hydrochloride are obtained as an oily substance. IR: 1647 cm$^{-1}$ (CO amide).

(J) 1.66 g of 2-[3-(N,N-dimethylamino)-propylaminocarbonyl]-3-hydroxy-1-phenylindole hydrochloride are dissolved in 25 ml dichloromethane and mixed successively under vigorous agitation with 0.6 ml of triethylamine and 0.3 ml of acetyl chloride. The reaction mixture is boiled for 30 min under reflux. After cooling, the mixture is washed with a small amount of a saturated solution of sodium chloride, the organic phase dried over sodium sulfate and evaporated under vacuum. Following recrystallization from isopropanol, 1.00 g (57% of theoretical) 2[3-(N,N-diethylamino)-propylaminocarbonyl]-3-acetoxy-1-phenylindole hydrochloride is obtained. Melting point: 174°-176° C.

IR spectrum: 1771 cm$^{-1}$, 1663 cm$^{-1}$

EXAMPLE 2

2-[3-(N,N-diethylamino)-2-hydroxypropylaminocarbonyl]-3-benzyloxy-1-phenylindole (A) 112 g of N-phenylindoxylic acid methylester (prepared according to Example 1, (A) to (F) are heated in 600 ml dimethylformamide with sodium ethylate (prepared from 16.6 g of sodium hydroxide and methanol) and 54 ml of benzyl bromide for 2 h under reflux. Subsequently, part of the dimethylformamide is distilled off, the remaining solution diluted with water and the N-phenyl-3-benzyloxyindole-2-carboxylic acid methylester suctioned off and heated for saponification with 19 g of sodium hydroxide in 600 ml of 50% ethanol for 2 h under reflux. The reaction mixture is dissolved in water, the aqueous phase acidified with hydrochloric acid and the N-phenyl-3-benzyloxyindole-2-carboxylic acid suctioned off.

(B) 10.5 g of N-phenyl-3-benzyloxyindole-2-carboxylic acid are reacted with 4.5 g of 2-chloro-N-pyridinium iodide, 4.2 ml of triethylamine and 2.5 g of 1-amino-2-hydroxy-3-diethylaminopropane in 45 ml of methylene chloride at room temperature, After 14 h, the reaction mixture is washed with a saturated solution of sodium chloride and with a 10% sodium carbonate solution, dried over sodium sulfate, filtered and evaporated. The residue is dissolved in dilute hydrochloric acid/ether and the ether phase separated. The aqueous phase is made alkaline and extracted with ether. The ether extract is washed with water, dried over sodium sulfate and evporated. The raw 2-[3-N,N-diethylamino)-2-hydroxypropylaminocarbonyl]-3-benzyloxy-1-phenylindole is recrystallized from isopropanol/ether. Melting point: 80°-81° C.

IR spectrum: 1647 cm$^{-1}$.

EXAMPLE 3

2-[3-(N,N-diethylamino)-2-hydroxypropylaminocarbonyl]-3-pivaloyloxy-1-phenylindole (A) An ether solution of N-phenyl-3-methoxy-indole-2-carboxylic acid obtained by the reaction of 92 g N-phenyl-3-methoxyindole-2-carboxylic acid with thionyl chloride and pyridine in ether according to Example 1H is added drop-wise to a solution of 579 g of 1-amino-2-hydroxy-3-diethylaminopropane and 40 g of triethylamine in 70 ml of methylene chloride under cooling with ice. The reaction mixture is agitated for 1 h at room temperature and subsequently processed as described in Example 1H. 110 g of 2-[3-(N,N-diethylamino)-2-hydroxypropylaminocarbonyl]-3- methoxy-1-phenylindole hydrochloride are obtained. Melting point: 148°-150° C.

(B) 15 g of 2-[3-(N,N-dimethylamino)-hydroxypropylaminocarbonyl]-3-methoxy-1-phenylindole hydrochloride are boiled with 15 ml of methanol and 15 ml of concentrated hydrochloric acid for 3 h under reflux. The reaction mixture is subsequently evaporated in vacuum. The 2-[3-(N,N-dimethylamino)-2-hydroxypropylaminocarbonyl]-3-hydroxy-1-phenylindole hydrochloride remaining has after recrystallization from isopropanol a melting point of 166°-168° C.

(C) 12.6 g of 2-[3-(N,N-diethylamino)-2-hydroxypropylaminocarbonyl]-3-hydroxy-1-phenylindole hydrochloride (0.03 mole) are mixed with 150 ml of methylene chloride, 4.2 ml of triethylamine (0.03 mole) and 3.9 ml of pivaloyl chloride (0.03 mole) and the reaction mixture allowed to stand for 3 h at room temperature. The mixture is subsequently washed with a saturated sodium chloride solution, dried over sodium sulfate and filtered. The solution is then evaporated, the residue dissolved in methylene chloride and purified by means of low pressure chromatography over silica gel acid. As the elution agent, first methylene chloride and subsequently methylene chloride containing 10% methanol are used. The 2-[3-(N,N-diethylamino)-2-hydroxypropylaminocarbonyl]-3-pivaloyloxy-1-phenylindole hydrochloride obtained as the residue after the evaporation of the eluate is then recrystallized from isopropanol. Melting point: 157°–159°.

IR spectrum: 1758 cm$^{-1}$, 1661 cm$^{-1}$.

EXAMPLE 4

2-[3-(N,N-diethylamino)-2-hydroxypropylaminocarbonyl]-3-benzoyloxy-1-phenylindole 2.1 g of 2-[3-(N,N-dimethylamino)-2-hydroxypropylamino-carbonyl]-3-hydroxy-1-phenylindole-hydrochloride (0.005 mole, prepared according to Example 3B) are reacted in 25 ml of anhydrons methylene chloride with 0.3 g (0.01 mole) of sodium hydride (80%). After 30 min 1.5 ml of benzoyl chloride (0.012 mole) are added cold and the reaction mixture allowed to stand for 16 h at room temperature. The solution is then filtered, washed with a saturated sodium chloride solution, dried over sodium sulfate and evaporated. The raw product obtained as the residue consists of a mixture of the hydrochlorides of 2-[3-N,N-diethylamino)-2-hydroxypropylaminocarbonyl]-3-benzoyloxy-1-phenylindole and 2-[3-(N,N-diethylamino)-2-benzoyloxypropylaminocarbonyl]-3-benzoyloxy-1-phenylindole. This raw product is dissolved in ethyl acetate and the solution diluted with diethylether, whereby the hydrochloride of 2-[3-(N,N-diethylamino)-2-hydroxypropylaminocarbonyl]-3-benzoyloxy-1-phenylindole is obtained in the crystalline form. After recrystallization from ethyl acetate/diethylether, it has a melting point of 130°–133° C.

IR spectrum: 1735 cm$^{-1}$, 1654 cm$^{-1}$.

EXAMPLE 5

2-[3-(N,N-Diethylamino)-2-acetoxypropylaminocarbonyl]-3-acetoxy-1-phenylindole 10.5 g 2-[3-(N,N-diethylamino)-2-hydroxypropylaminocarbonyl]-3-hydroxy-1-phenylindole hydrochloride (0.0025 mole) are mixed with 100 ml of methylene chloride and 7.0 ml of triethyleneamine (0.05 mole). Subsequently, 3.6 ml of acetyl chloride (0.05 mole) are added to the reaction solution and the reaction mixture allowed to stand for 18 hours at room temperature. The solution is then washed with a saturated solution of sodium chloride, dried over sodium sulfate, filtered and evaporated. The raw product remaining as the residue is purified by low pressure chromatography as described in Example 3. 2-[3-(N,N-diethylamino)-2-acetoxypropylaminocarbonyl]-3-acetoxy-1-phenylindole hydrochloride is obtained as an oily product. IR spectrum: 1778 cm$^{-1}$, 1741 cm$^{-1}$.

EXAMPLE 6

2-[3-(N,N-Diethylamino)-2-hydroxypropylaminocarbonyl]-3-methoxycarbonylethylcarbonyloxy-1-phenylindole 2.1 g of 2-[3-(N,N-diethylamino)-2-hydroxypropylaminocarbonyl]-3-hydroxy-1-phenylindole hydrochloride (0.005 mole) are mixed in 25 ml of methylene chloride with 0.7 ml triethylamine (0.005 mole) and 0.6 ml of succinic acid methylester chloride and the reaction mixture agitated for 1 h at room temperature. The solution is then washed with a saturated solution of sodium chloride, dried over sodium sulfate, filtered and evaporated. The residue is purified by low pressure chromatography using methylene chloride as the elution agent, as described in Example 3. 2-[3-N,N-diethylamino)-2-hydroxypropylaminocarbonyl]-3-methoxycarbonylethylcarbonyloxy-1-phenylindole hydrochloride is obtained as an oily product.

IR spectrum: 1768 cm$^{-1}$, 1734 cm$^{-1}$, 1654 cm$^{-1}$.

The compounds of Formula I listed in the following table also may be prepared by the processes described in Examples 1 to 6, by the acylation of the corresponding compounds of Formula II or by amidization of the corresponding compounds of Formula Va.

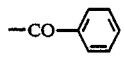

| EXAMPLE NO. | $R_3$ | $R_4$ | $R_5$ | $R_6$ | $R_2$ | Z | $R_7$ | $R_8$ | $R_1$ | NOTES: Mp in °C., HCl = Hydrochloride IR-BANDS in cm$^{-1}$ |
|---|---|---|---|---|---|---|---|---|---|---|
| 7 | H | H | H | H | H | $CH_2-CH_2-CH_2$ | $C_2H_5$ | $C_2H_5$ | $-CO-\phenyl$ | HCl, Fp. 190–192 IR: 1736, 1662 |
| 8 | H | H | 4-Cl | H | H | $CH_2-CH_2$ | $CH_3$ | $CH_3$ | $-CO-C(CH_3)_3$ | HCl, Fp. 215–217 IR: 1761, 1663 |
| 9 | H | H | 4-Cl | H | H | $CH_2-CH_2-CH_2$ | $CH_3$ | $CH_3$ | $-CO-C(CH_3)_3$ | HCl, oily IR: 1751, 1653 |
| 10 | H | H | 2,3-di-$CH_3$ | H | H | $CH_2-CH_2$ | $CH_3$ | $CH_3$ | $-CO-C(CH_3)_3$ | HCl, Fp. 118–120 IR: 1752, 1663 |
| 11 | 5-Br | H | H | H | H | $CH_2-CH_2$ | $CH_3$ | $CH_3$ | $-CO-C(CH_3)_3$ | HCl, Fp. 210–212 IR: 1758, 1652 |

-continued

| EXAMPLE NO. | R3 | R4 | R5 | R6 | R2 | Z | R7 | R8 | R1 | NOTES: Mp in °C., HCl = Hydrochloride IR-BANDS in cm$^{-1}$ |
|---|---|---|---|---|---|---|---|---|---|---|
| 12 | H | H | 4-Cl | H | H | CH$_2$—CH(OH)—CH$_2$ | C$_2$H$_5$ | C$_2$H$_5$ | —CO—C(CH$_3$)$_3$ | HCl, oily IR: 1752, 1663 |
| 13 | H | H | 4-CH$_3$O | H | H | CH$_2$—CH(OH)—CH$_2$ | C$_2$H$_5$ | C$_2$H$_5$ | —CO—C(CH$_3$)$_3$ | HCl, oily IR: 1757, 1653 |
| 14 | H | H | 4-F | H | H | CH$_2$—CH(OH)—CH$_2$ | C$_2$H$_5$ | C$_2$H$_5$ | —CO—C(CH$_3$)$_3$ | HCl, Fp. 183–185 IR: 1756, 1663 |
| 15 | H | H | 4-F | H | H | CH$_2$—CH(OH)—CH$_2$ | C$_2$H$_5$ | C$_2$H$_5$ | —CO—C$_6$H$_5$ | HCl, Fp. 186–188 IR: 1741, 1662 |
| 16 | H | H | 4-Cl | H | H | CH$_2$—CH(OH)—CH$_2$ | C$_2$H$_5$ | C$_2$H$_5$ | —CO—C$_6$H$_5$ | HCl, Fp. 190–194 IR: 1743, 1658 |
| 17 | H | H | H | H | H | CH$_2$—CH(OH)—CH$_2$ | C$_2$H$_5$ | C$_2$H$_5$ | —CO—C$_6$H$_4$—NO$_2$ | HCl, oily, IR: 1749, 1653 |
| 18 | H | H | H | H | H | CH$_2$—CH(OH)—CH$_2$ | C$_2$H$_5$ | C$_2$H$_5$ | —CO—C$_6$H$_4$—CH$_3$ | HCl, oily IR: 1734, 1653 |
| 19 | H | H | H | H | H | CH$_2$—CH(OH)—CH$_2$ | C$_2$H$_5$ | C$_2$H$_5$ | —CO—C$_6$H$_4$—OCH$_3$ | HCl, oily IR: 1734, 1654 |
| 20 | H | H | H | H | H | CH$_2$—CH(OH)—CH$_2$ | C$_2$H$_5$ | C$_2$H$_5$ | —CO—n-C$_{11}$H$_{23}$ | HCl, oily IR: 1765, 1653 |
| 21 | H | H | H | H | H | CH$_2$—CH(O—CO—C$_6$H$_5$)—CH$_2$ | C$_2$H$_5$ | C$_2$H$_5$ | —CO—C$_6$H$_5$ | HCl, Fp. 173–175 IR: 1744, 1725, 1669 |
| 22 | H | H | H | H | H | CH$_2$—CH(O—CO—C$_6$H$_4$—CH$_3$)—CH$_2$ | C$_2$H$_5$ | C$_2$H$_5$ | —CO—C$_6$H$_4$—CH$_3$ | HCl, oily IR: 1744, 1717, 1669 |
| 23 | H | H | 4-Cl | H | H | CH$_2$—CH(O—CO—C$_6$H$_5$)—CH$_2$ | C$_2$H$_5$ | C$_2$H$_5$ | —CO—C$_6$H$_5$ | HCl, Fp. 127–129 IR: 1741, 1720, 1669 |
| 24 | H | H | H | H | H | CH$_2$—CH(OH)—CH$_2$ | C$_2$H$_5$ | C$_2$H$_5$ | —C$_6$H$_4$—CH$_3$ | HCl, oily IR: 1647 |
| 25 | H | H | H | H | H | CH$_2$—CH(OH)—CH$_2$ | C$_2$H$_5$ | C$_2$H$_5$ | —C$_6$H$_4$—Cl | Base, oil IR: 1658 |
| 26 | H | H | H | H | H | CH$_2$—CH(OH)—CH$_2$ | C$_2$H$_5$ | C$_2$H$_5$ | —C$_6$H$_4$—NO$_2$ | Base, oil IR: 1647 |
| 27 | H | H | H | H | H | CH$_2$—CH(OH)—CH$_2$ | C$_2$H$_5$ | C$_2$H$_5$ | —C$_6$H$_4$—Cl (2-Cl) | Base, oil IR: 1647 |

EXAMPLE I: Tablets

Tablets are prepared with the following composition per tablet: 2-[3-(N,N-diethylamino)-2-hydroxypropylaminocarbonyl]-3-pivaloyl-1-phenylindole hydrochloride 15 mg, corn starch 60 mg, lactose 140 mg, gelatin 6 mg (as a 10% solution).

The active ingredient, the cornstarch, and the lactose are worked into a paste with the 10% gelatin solution. The paste is comminuted and the resulting granules placed on a suitable metal sheet and dried at 45° C. The dry granules are passed into a comminuting machine and mixed in a mixer with the following auxiliary substances:

talcum: 5 mg
magnesium stearate: 5 mg
corn starch: 9 mg and pressed into 240 mg tablets.

What is claimed is:

1. A 1-phenyl-2-aminocarbonylindole compound and the acid addition salts thereof, said compound having the formula

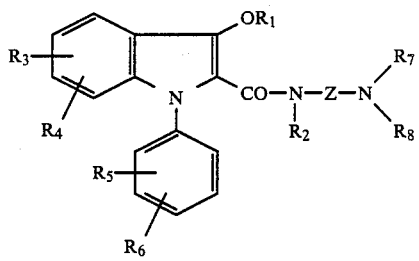

(I)

wherein
$R_1$ is selected from the group of
(i) an alkanoyl group with 2 to 12 carbon atoms which is unsubstituted or is substituted by a carboxyl group, a lower alkoxycarbonyl group, a lower alkoxy radical, or a benzyloxy radical;
(ii) a group a having the formula

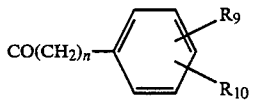

a wherein
(a) n is 0, 1, 2, or 3,
($b_1$) $R_9$ is a hydrogen, a halogen, a lower alkyl radical, or a lower alkoxy radical and
(c) $R_{10}$ is a hydrogen, a halogen, a lower alkyl radical, or, when n is 0 and $R_9$ is hydrogen, nitro or trifluoromethyl, or
($b_2$) $R_9$ and $R_{10}$, if attached to adjacent carbon atoms, together represent a methylenedioxy radical; and
(iii) a benzyl radical which is unsubstituted or is substituted by one or two substituents from the group consisting of a lower alkyl radical, a lower alkoxy radical, a nitro, and a halogen,
$R_2$ is a hydrogen or a lower alkyl radical,
$R_3$, $R_4$ and $R_5$ are separately a hydrogen, a halogen, a lower alkyl radical or lower alkyoxy radical,
$R_6$ is a hydrogen, a halogen, a lower alkyl radical, a lower alkoxy radical, or if $R_5$ is hydrogen, a nitro or trifluoromethyl,
$R_7$ and $R_8$ are separately a hydrogen or a lower alkyl radical, or $R_7$ and $R_8$ together with the nitrogen atom to which both are attached denote a heterocyclic group b having the formula

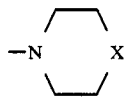

b wherein
X represents a bond, —$CH_2$—, —$C_2H_4$—, O r S, and
Z is an alkylene chain with 2 to 5 carbon atoms which is unsubstituted or is substituted at a carbon atom not attached to nitrogen atom by a hydroxy radical or an $R_1'O$ group, wherein $R_1'$ is defined as is $R_1$ but excepting the unsubstituted or substituted benzyl radical.

2. A 1-phenyl-2-aminocarbonylindole compound according to claim 1, wherein $R_2$ is hydrogen.

3. A 1-phenyl-2-aminocarbonylindole compound according to claim 1, wherein $R_1$ is an alkanoyl group with 2 to 12 carbon atoms which is substituted by a carboxyl group, a lower alkoxycarbonyl group, a lower alkoxy radical, or a benzyloxy radical.

4. A 1-phenyl-2-aminocarbonylindole compound according to claim 1, wherein $R_1$ is a benzyl radical which is unsubstituted or is substituted by one or two substituents from the group consisting of a lower alkyl radical, a lower alkoxy radical, a nitro and a halogen.

5. A 1-phenyl-2-aminocarbonylindole compound according to claim 1, wherein Z is an alkylene chain with 2 to 5 carbon atoms which is substituted at a carbon atom not attached to a nitrogen atom by a hydroxy radical or an $R'_1O$ group.

6. A 1-phenyl-2-aminocarbonylindole compound according to claim 1, wherein $R_1$ is an alkanoyl group with 2 to 12 carbon atoms which is unsubstituted or is substituted by a carboxyl group, a lower alkoxycarbonyl group, a lower alkoxy radical, or a benzyloxy radical.

7. A 1-phenyl-2-aminocarbonylindole compound according to claim 1, wherein $R_7$ and $R_8$ are separately a hydrogen or a lower alkyl radical.

8. A 1-phenyl-2-aminocarbonylindole compound according to claim 1, wherein $NR_7R_8$ together represents a straight-chain dialkylamino group.

9. A 1-phenyl-2-aminocarbonylindole compound according to claim 1, wherein $R_1$ is defined as in claim 1 but excluding said unsubstituted or substituted benzyl radical, $R_2$ is a hydrogen, $R_3$ and $R_4$ are separately a hydrogen or a halogen, $R_5$ and $R_6$ are separately a hydrogen, a halogen, or a lower alkyl radical, and $R_7$ and $R_8$ are separately a hydrogen or a lower alkyl radical.

10. A 1-phenyl-2-aminocarbonylindole compound according to claim 9, wherein Z is an alkylene chain with 2 to 5 carbon atoms which is substituted at a carbon atom not attached to a nitrogen atom by a hydroxy radical or an $R'_1O$ group.

11. A 1-phenyl-2-aminocarbonylindole compound according to claim 10, wherein $R_2$ to $R_6$ are hydrogen.

12. A 1-phenyl-2-aminocarbonylindole compound according to claim 1, wherein $R_1$ is an alkanoyl group with 2 to 5 carbon atoms.

13. A 1-phenyl-2-aminocarbonylindole compound according to claim 1, wherein $R_1$ is a group a having the formula

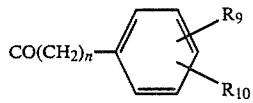

wherein:
(a) n is 0 or 1,
(b) $R_9$ is a hydrogen, a halogen, a lower alkyl radical, or a lower alkoxy radical, and
(c) $R_{10}$ is a hydrogen, a halogen, a lower alkyl radical, lower alkoxy radical, or, when n is 0 and $R_9$ is hydrogen, nitro or trifluoromethyl.

14. A 1-phenyl-2-aminocarbonylindole compound according to claim 9, wherein $R_1$ is an alkanoyl radical with 2 to 5 carbon atoms.

15. A 1-phenyl-2-aminocarbonylindole compound according to claim 9, wherein $R_1$ is a group a having the formula:

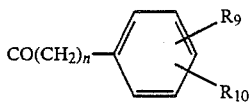

wherein:
(a) n is 0 or 1,
(b) $R_9$ is a hydrogen, a halogen, a lower alkyl radical, or a lower alkoxy radical, and
(c) $R_{10}$ is a hydrogen, a halogen, a lower alkyl radical, lower alkoxy radical, or, when n is 0 and $R_9$ is hydrogen, nitro or trifluoromethyl.

16. A 1-phenyl-2-aminocarbonoylindole compound according to claim 1, wherein $R_2$ $R_3$, $R_4$, $R_5$ and $R_6$ all represent hydrogen, $R_7$ and $R_8$ both represent ethyl, Z is a 2-hydroxypropylene group, and $R_1$ represents pivaloyl or benzoyl.

17. A 1-phenyl-2-aminocarbonylindole compound according to claim 1, wherein $R_2$ to $R_6$ are all hydrogen, $R_7$ and $R_8$ are both ethyl, Z is a 2-hydroxypropylene group or a $R'_10$ propylene group, and $R_1$ represents acetyl, propionyl, isobutyryl, pivaloyl, dodecanoyl, benzoyl, chlorobenzoyl, nitrobenzoyl, methylbenzoyl, methoxybenzoyl, or phenylacetyl.

18. A pharmaceutical preparation comprising a physiologically compatible carrier and a heart rhythm regulating effective quantity of a 1-phenyl-2-aminocarbonylindole compound according to claim 1.

* * * * *